US008879689B2

(12) United States Patent
Ohta et al.

(10) Patent No.: US 8,879,689 B2
(45) Date of Patent: Nov. 4, 2014

(54) RADIOGRAPHIC IMAGE DETECTING DEVICE AND CONTROL METHOD THEREOF

(71) Applicant: FUJIFILM Corporation, Tokyo (JP)

(72) Inventors: Yasunori Ohta, Ashigarakami-gun (JP); Kouichi Kitano, Ashigarakami-gun (JP); Naoyuki Nishino, Ashigarakami-gun (JP); Haruyasu Nakatsugawa, Ashigarakami-gun (JP); Naoto Iwakiri, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 14/094,234

(22) Filed: Dec. 2, 2013

(65) Prior Publication Data

US 2014/0086391 A1 Mar. 27, 2014

Related U.S. Application Data

(63) Continuation of application No. PCT/JP2012/068671, filed on Jul. 24, 2012.

(30) Foreign Application Priority Data

Jul. 26, 2011 (JP) ................................. 2011-163194

(51) Int. Cl.
*H05G 1/46* (2006.01)
*H04N 5/374* (2011.01)
*A61B 6/00* (2006.01)
*H04N 5/32* (2006.01)
*H04N 5/235* (2006.01)
*H04N 5/353* (2011.01)

(52) U.S. Cl.
CPC ............... *A61B 6/542* (2013.01); *H04N 5/374* (2013.01); *A61B 6/4283* (2013.01); *A61B 6/4233* (2013.01); *H04N 5/32* (2013.01); *H04N 5/2351* (2013.01); *H04N 5/353* (2013.01)
USPC ............................................. 378/97; 378/108

(58) Field of Classification Search
USPC .................................... 378/97, 108, 110, 112
See application file for complete search history.

(56) References Cited

U.S. PATENT DOCUMENTS 6,404,851 B1 6/2002 Possin et al.
2002/0050568 A1 5/2002 Nonaka
(Continued)

FOREIGN PATENT DOCUMENTS

JP 11-151233 A 6/1999
JP 11-155847 A 6/1999
(Continued)

OTHER PUBLICATIONS

International Preliminary Report on Patentability, and Translation of Written Opinion of the International Searching Authority (Forms PCT/IB/338, PCT/IB/373 and PCT/ISA/237) dated Feb. 6, 2014 for International Application No. PCT/JP2012/068671.
International Search Report issued in PCT/JP2012/068671, dated Oct. 2, 2012.

*Primary Examiner* — Hoon Song
(74) *Attorney, Agent, or Firm* — Birch, Stewart, Kolasch & Birch, LLP

(57) ABSTRACT

An X-ray image detecting device has an FPD having a matrix of pixels each for accumulating signal charge in accordance with an X-ray irradiation amount. An imaging area of the FPD is partitioned into a plurality of divided sections A to I. Each of the divided sections A to I has a short pixel for detecting X-ray irradiation. In a synchronization control for controlling the FPD in synchronization with detection of a start of X-ray emission from an X-ray source, a control unit for controlling the X-ray image detecting device uses all the divided sections A to I. In an automatic exposure control for stopping the X-ray emission from the X-ray source by detecting a total X-ray irradiation amount, the control unit uses part of the divided sections, e.g. the short pixels of the divided sections that are judged to be opposed to an object in the synchronization control.

19 Claims, 11 Drawing Sheets

(56) References Cited

U.S. PATENT DOCUMENTS

| | | |
|---|---|---|
| 2002/0101527 A1 | 8/2002 | Endo |
| 2003/0081823 A1 | 5/2003 | Nonaka |
| 2007/0297569 A1* | 12/2007 | Saunders ............... 378/108 |
| 2008/0226024 A1* | 9/2008 | Strommer ................. 378/37 |
| 2008/0240346 A1* | 10/2008 | Kashiwagi et al. ......... 378/37 |

FOREIGN PATENT DOCUMENTS

| | | |
|---|---|---|
| JP | 2002-590 A | 1/2002 |
| JP | 2002-181942 A | 6/2002 |
| JP | 2003-529425 A | 10/2003 |
| JP | 2010-214056 A | 9/2010 |
| JP | 2011-10870 A | 1/2011 |

* cited by examiner

RADIOGRAPHIC IMAGE DETECTING DEVICE AND CONTROL METHOD THEREOF

CROSS REFERENCE TO RELATED APPLICATIONS

This application is a Continuation of PCT International Application No. PCT/JP2012/068671 filed on Jul. 24, 2012, which claims priority under 35 U.S.C. §119(a) to Patent Application No. 2011-163194 filed in Japan on Jul. 26, 2011, all of which are hereby expressly incorporated by reference into the present application.

BACKGROUND OF THE INVENTION

1. Field of the Invention

The present invention relates to a radiographic image detecting device for detecting a radiographic image of an object and a control method thereof.

2. Description Related to the Prior Art

In a medical field, for example, an X-ray image capturing system using X-rays as a kind of radiation is known. The X-ray image capturing system is constituted of an X-ray generating device having an X-ray source for emitting the X-rays, and an X-ray image detecting device for detecting an X-ray image, which represents image information of an object, by receiving application of the X-rays that have been emitted from the X-ray source and transmitted through the object. The X-ray source is provided with a tube current for determining an X-ray dose per unit of time and a tube voltage for determining X-ray quality (energy spectrum), as an imaging condition. The imaging condition is determined whenever imaging is performed, in accordance with a body part to be imaged, the age, and the like of an examinee being the object. The X-ray source radiates the X-rays in accordance with the set imaging condition.

A type of X-ray image detecting device that uses an X-ray image detector (flat panel detector (FPD)), instead of a conventional X-ray film or imaging plate (IP), is in practical use (refer to Japanese Patent Laid-Open Publication No. 2010-214056). The FPD is constituted of a detection panel and a signal processing circuit. The detection panel has an imaging area in which a plurality of pixels each for accumulating signal charge in accordance with an X-ray irradiation amount are arranged in a matrix and signal lines connected to the pixels are laid out to read the signal charge from the pixels. The signal processing circuit reads the signal charge accumulated in each pixel as a voltage signal, and converts the read voltage signal into digital image data. Thus, the X-ray image detecting device using the FPD allows an observation of the X-ray image immediately following the taking of the X-ray image.

In the detection panel, each of the pixels provided in the imaging area is constituted of a photodiode, being a photoelectric conversion element, and a TFT (thin film transistor). A scintillator (phosphor) is provided on the imaging area to convert the X-rays into visible light. The TFT is a switching element that switches the operation of the pixel by the electrical connection and disconnection between the photodiode and the signal line. Upon turning off the TFT, the photodiode is disconnected from the signal line, and an accumulation operation for accumulating the signal charge to the photodiode is started. Upon turning on the TFT, the photodiode is connected to the signal line, and a readout operation for reading the signal charge from the photodiode through the TFT and the signal line is started.

In contrast to the X-ray film and the IP, the FPD requires a synchronous control in order to start the accumulation operation and the readout operation in synchronization with X-ray emission timing. As a synchronous control method, there are a method of communicating a synchronous signal between the X-ray generating device and the X-ray image detecting device, a method of determining emission start timing and emission stop timing by detecting an X-ray irradiation amount, and the like.

The Japanese Patent Laid-Open Publication No. 2010-214056 discloses that the X-ray irradiation amount is detected by an X-ray detection means provided in the imaging area of the FPD, and is used in various types of control. More specifically, taking advantage of the fact that X-ray irradiation causes variations in a bias current flowing through a bias line for applying a bias voltage to the photodiodes, the start and stop of X-ray emission are detected. The synchronization control, that is, the FPD is controlled in synchronization with the detection of the start and stop of X-ray emission is performed. The Japanese Patent Laid-Open Publication No. 2010-214056 also discloses an automatic exposure control (AEC) in which a total X-ray irradiation amount is measured based on the variations in the bias current, and the X-ray source stops emitting the X-rays when the total X-ray irradiation amount has reached a predetermined threshold value.

The bias lines are connected to all the pixels in the imaging area of the FPD. Thus, according to the FPD of the Japanese Patent Laid-Open Publication No. 2010-214056, the synchronization control and the automatic exposure control are performed by monitoring variations in the bias current using the entire imaging area as a detection area, and using one or more of divided sections into which the imaging area is divided as a detection area. In either of cases where the entire imaging area is assigned as the detection area and the divided section is assigned as the detection area, both the synchronization control and the automatic exposure control use the same detection area.

The object is positioned with respect to the imaging area of the FPD when taking the X-ray image. In a case where the object is smaller than the imaging area in size and is not opposed to the entire imaging area, like a hand or a foot, for example, the X-ray irradiation amount differs from place to place within the imaging area. To be more specific, a part of the imaging area that is not opposed to the object becomes a directly exposed area to which the X-rays are directly applied without passing through the object. The X-ray irradiation amount is large in the directly exposed area because of no absorption of the X-rays by the object. On the other hand, a part of the imaging area that is opposed to the object is irradiated with the X-rays passed through the object, so the X-ray irradiation amount is small due to absorption of the X-rays by the object.

Also, as shown in FIG. 12, in a graph in which a horizontal axis represents time and a vertical axis represents the X-ray irradiation amount, the X-ray irradiation amount gradually increases from the start of X-ray emission. The X-ray irradiation amount has reached a predetermined value, and then is kept at the value for a while until the stop of X-ray emission. As shown by a solid line in the drawing, the X-ray irradiation amount of the directly exposed area sharply rises and quickly reaches the threshold value because of no X-ray absorption by the object. On the other hand, more time is required by the X-ray irradiation amount of the area opposed to the object for reaching the threshold value, as shown by a broken line in the drawing, due to the X-ray absorption by the object. Thus, using the area opposed to the object as the detection area requires longer detection time, as compared with the case of using the directly exposed area as the detection area. This also causes high susceptibility to noise because of a low output value of a signal in accordance with the low X-ray irradiation amount, and low detection accuracy. In the synchronization control, it is desirable to be able to certainly detect a rise of the X-rays in a short time, so the directly exposed area is preferably used as the detection area for the synchronization control.

On the other hand, out of the imaging area of the FPD, the area opposed to the object is preferably used as the detection area in measuring the total X-ray irradiation amount in the automatic exposure control. This is because if the total X-ray irradiation amount of the directly exposed area is measured in the automatic exposure control, the measured total X-ray irradiation amount reaches the threshold value before a required amount of X-rays is applied to the object. This results in underexposure of the X-ray image.

According to the Japanese Patent Laid-Open Publication No. 2010-214056, the same detection area is used in both the synchronization control and the automatic exposure control. Accordingly, if most of the detection area is the directly exposed area, the underexposure may occur in the automatic exposure control, though the accuracy of the synchronization control is increased. On the contrary, if most of the detection area is opposed to the object, the accuracy of the synchronization control is reduced, though the accuracy of the automatic exposure control is increased.

SUMMARY OF THE INVENTION

An object of the present invention is to provide a radiographic image detecting device that can perform an accurate synchronization control with timing of the start of radiation emission and an accurate automatic exposure control for controlling a total radiation irradiation amount, and a control method of the radiographic image detecting device.

To achieve the above object, a radiographic image detecting device according to the present invention includes an image detector, radiation detectors, and a control unit. The image detector has an imaging area having a matrix of a plurality of pixels each for accumulating signal charge in accordance with an irradiation amount of radiation emitted from a radiation source. The image detector detects a radiographic image by receiving the radiation passed through an object. The radiation detector outputs a detection signal in accordance with the irradiation amount of the radiation. There are a plurality of radiation detectors disposed in the imaging area. The control unit performs a synchronization control for synchronizing an operation of the image detector with emission start timing of the radiation based on the detection signal of the radiation detector, and an automatic exposure control for controlling a total irradiation amount of the radiation based on the detection signal of the radiation detector. The detection signal of the radiation detector disposed in a first detection area in the imaging area is used in the synchronization control. The detection signal of the radiation detector disposed in a second detection area smaller than the first detection area is used in the automatic exposure control.

The second detection area is preferably included in the first detection area. The control unit preferably designates the second detection area based on the detection signals outputted from the plurality of radiation detectors disposed in the first detection area. The control unit preferably designates the second detection area by using the detection signal read in the synchronization control.

The control unit preferably compares the detection signals outputted from the plurality of radiation detectors disposed in the first detection area, and judges a section having the radiation detector that outputs a relatively low detection signal as a section opposed to the object, and designates the section opposed to the object as the second detection area.

The imaging area is preferably composed of a plurality of divided sections each having the radiation detector. The first detection area is preferably composed of a combination of the divided sections, and the second detection area is preferably composed of another combination of the divided sections.

Each of the divided sections preferably has a same number of radiation detectors. Note that, the same number includes substantially the same number, in addition to exactly the same number.

In the synchronization control, the control unit preferably monitors a start of emission of the radiation from the radiation source based on the detection signal of the radiation detector disposed in the first detection area, and makes the image detector start accumulating the signal charge upon detecting the start of emission of the radiation from the radiation source.

In the synchronization control, the control unit preferably detects the start of emission, when one of the detection signals of the plurality of radiation detectors disposed in the first detection area has exceeded a threshold value.

In the automatic exposure control, the control unit preferably measures a total irradiation amount of the radiation by integrating the detection signal of the radiation detector, and makes the radiation source stop emitting the radiation when the total irradiation amount has reached a threshold value. When the total irradiation amount of the radiation has reached the threshold value, the control unit preferably ends accumulation of the signal charge by the image detector.

In the automatic exposure control, the control unit preferably measures a total irradiation amount of the radiation by integrating the detection signal of the radiation detector, and controls a gain in reading the signal charge from the pixel based on the total irradiation amount.

The radiation detector is a short pixel in which the pixel and a signal line for reading the signal charge from the pixel are always short out, and the short pixel always outputs to the signal line the signal charge in accordance with the irradiation amount of the radiation.

The radiation detector may be a photosensor array stacked on the image detector. The photosensor array has a plurality of detection elements for outputting the detection signal in accordance with the irradiation amount of the radiation. The photosensor array is preferably made of an organic photoelectric conversion material. The photosensor array may be disposed on a side of the radiation source with respect to the imaging area.

The radiographic image detecting device preferably allows taking a moving image, in addition to a still image. The radiation source may continuously emit a plurality of radiation pulses. The control unit may perform the synchronization control and the automatic exposure control on a pulse-by-pulse basis.

According to a control method of a radiographic image detecting device of the present invention, the radiographic image detecting device has an imaging area having a matrix of a plurality of pixels each for accumulating signal charge in accordance with an irradiation amount of radiation emitted from a radiation source, and the radiographic image detecting device detects a radiographic image by receiving the radiation passed through an object. In the control method, a synchronization control for synchronizing an operation of the radiographic image detecting device with emission start timing of the radiation based on a detection signal of a radiation detector disposed in a first detection area of the imaging area is performed. An automatic exposure control for controlling a total irradiation amount of the radiation based on the detection signal of the radiation detector disposed in a second detection area smaller than the first detection area is performed.

According to the present invention, the first detection area used in the synchronization control is relatively large in size, while the second detection area used in the automatic exposure control is relatively small in size. The larger the first detection area, the likelier it becomes that the first detection area includes a directly exposed area, which is not opposed to the object. Performing the synchronization control based on the detection signal of the directly exposed area allows increase in the accuracy of the synchronization control. On the other hand, since the automatic exposure control uses the second detection area, which is a part of the first detection area used in the synchronization control and smaller than the first detection area, the directly exposed area tends to be excluded from the second detection area. Performing the automatic exposure control based on the detection signal of the area opposed to the object allows increase in the accuracy of the automatic exposure control. Therefore, according to the present invention, it is possible to provide the radiographic image detecting device that can perform the accurate synchronization control with timing of the start of radiation emission and the accurate automatic exposure control for controlling the total radiation irradiation amount, and the control method of the radiographic image detecting device.

BRIEF DESCRIPTION OF THE DRAWINGS

For more complete understanding of the present invention, and the advantage thereof, reference is now made to the subsequent descriptions taken in conjunction with the accompanying drawings, in which.

DESCRIPTION OF THE PREFERRED EMBODIMENTS (First Embodiment)

Figure 1:
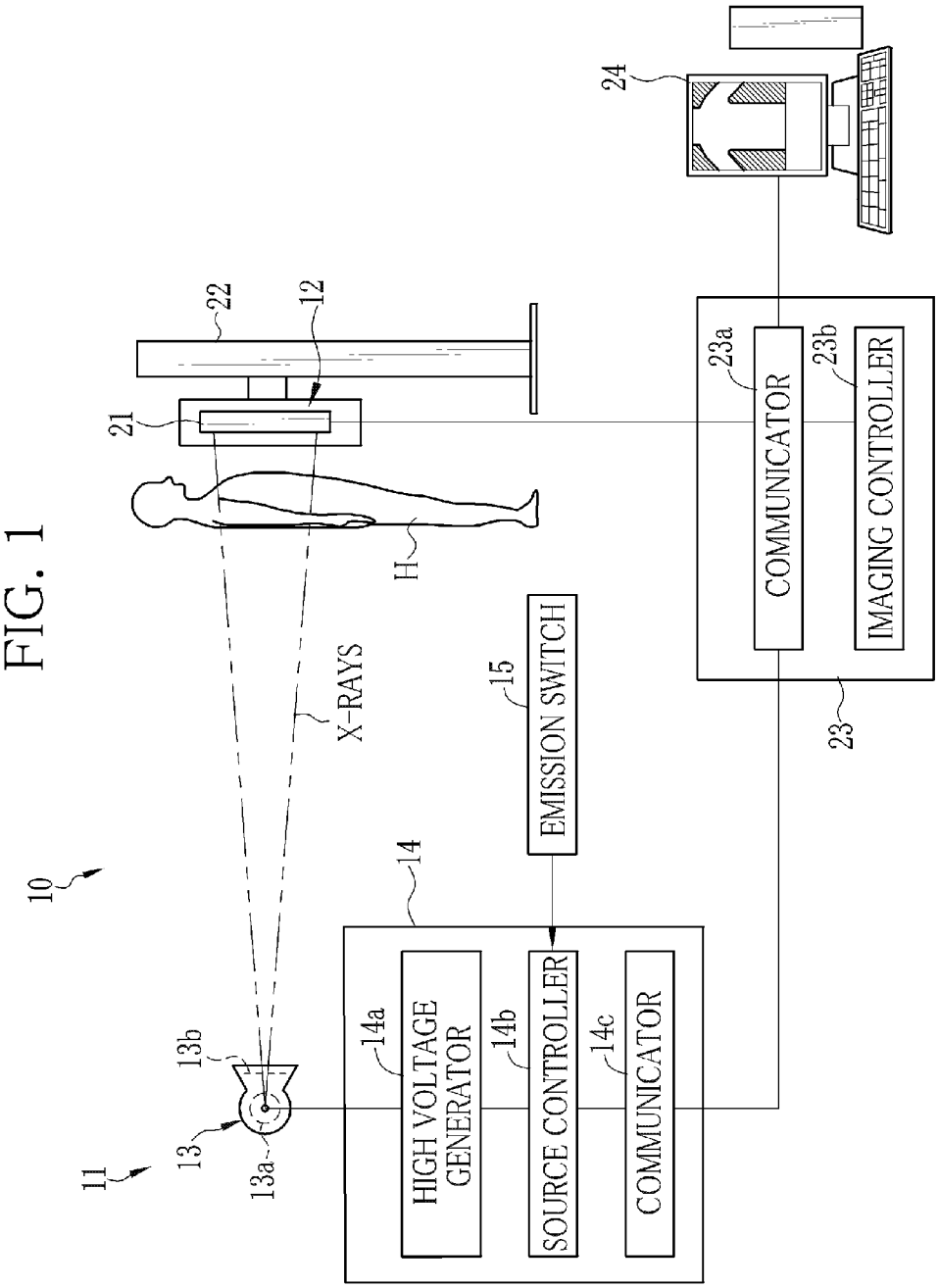
FIG. 1 is an explanatory view showing the schematic structure of an X-ray image capturing system.

In FIG. 1, an X-ray image capturing system 10 is constituted of an X-ray generating apparatus 11 and an X-ray imaging apparatus 12. The X-ray generating apparatus 11 includes an X-ray source 13, a source control unit 14 for controlling the X-ray source 13, and an emission switch 15. The X-ray source 13 has an X-ray tube 13a for emitting X-rays, and an irradiation field limiter (collimator) 13b for limiting an irradiation field of the X-rays radiating from the X-ray tube 13a.

The X-ray tube 13a has a cathode made of a filament for emitting thermoelectrons, and an anode (target) for radiating the X-rays by collision of the thermoelectrons emitted from the cathode. The irradiation field limiter 13b has, for example, four lead plates for blocking the X-rays. The four lead plates form a rectangular irradiation opening for transmitting the X-rays therethrough. Shifting the positions of the lead plates varies the size of the irradiation opening and restricts an irradiation field. The four lead plates are grouped in two pairs, and the two lead plates included in each pair are opposed to each other. The two pairs of the lead plates are disposed in two directions orthogonal to each other so as to form the rectangular irradiation opening.

The source control unit 14 includes a high voltage generator 14a, a source controller 14b, and a communicator 14c. The high voltage generator 14a supplies a high voltage to the X-ray source 13. The source controller 14b controls a tube voltage for determining the radiation quality (energy spectrum) of the X-rays emitted from the X-ray source 13, a tube current for determining a radiation dose per unit of time, and an X-ray emission time. The communicator 14c is communicatable with an imaging control unit 23 using a wired or wireless method. The high voltage generator 14a generates a high tube voltage by multiplying an input voltage by a transformer, and supplies the X-ray source 13 with a drive power through a high voltage cable. An imaging condition including the tube voltage, the tube current, and the like is set manually by an operator such as a radiological technician on the source controller 14b through an operation panel of the source control unit 14.

The emission switch 15 is connected to the source control unit 14 through a signal cable. The emission switch 15 is a two-step press switch to be operated by the radiological technician. Upon a half press of the emission switch 15, a warm-up start signal is issued to start warming up the X-ray source 13. Upon a full press, an emission start signal is issued to start an X-ray emission from the X-ray source 13. These signals are inputted to the source control unit 14 through the signal cable.

The source controller 14b controls the operation of the X-ray source 13 based on the control signals from the emission switch 15. Upon receiving the emission start signal from the emission switch 15, the source controller 14b issues an actuation command to the X-ray source 13 to start an electric power supply. Thus, the X-ray source 13 starts the X-ray emission. Upon inputting a stop signal from the imaging control unit 23 to the communicator 14c, the source controller 14b issues a stop command to the X-ray source 13 to stop the electric power supply, in order to synchronize the stop of X-ray emission with an end of an accumulation operation of an FPD 36. Upon receiving the stop command, the X-ray source 13 stops the X-ray emission.

An imaging support 22 has a slot into which a film cassette or an IP cassette is detachably insertable. The imaging support 22 is installed such that its X-ray incident surface is opposed to the X-ray source 13. Note that, an upright imaging support for imaging an examinee H in a standing position is shown as the imaging support 22 in the drawing, but the imaging support 22 may be an imaging table that images the examinee H in a lying position instead.

The X-ray imaging apparatus 12 includes an X-ray image detecting device 21, an imaging control unit 23, and a console 24. The X-ray image detecting device 21 is constituted of the FPD 36 (see FIG. 3) and a portable housing containing the FPD 36. The X-ray image detecting device 21, being a portable radiographic image detecting device, receives the X-rays that have been emitted from the X-ray source 13 and passed through the examinee (object) H and detects an X-ray image of the examinee H. The X-ray image detecting device 21 has the approximately rectangular flat housing in plane shape, and its plane size is approximately the same as those of the film cassette and the IP cassette so as to be attachable to the imaging support 22.

The imaging control unit 23 has a communicator 23a for wiredly or wirelessly communicating with the X-ray generating apparatus 11, the X-ray image detecting device 21, and the console 24, and an imaging controller 23b for controlling the X-ray image detecting device 21 through the communicator 23a. The imaging controller 23b sends the imaging condition to the X-ray image detecting device 21 to set up a signal processing condition of the FPD 36. For synchronization between the end of the accumulation operation of the FPD 36 and the stop of X-ray emission, the imaging control unit 23 sends the stop signal transmitted from the X-ray image detecting device 21 to the source control unit 14. Furthermore, the imaging controller 23b receives image data outputted from the X-ray image detecting device 21 through the communicator 23a, and sends the image data to the console 24.

The console 24 receives an entry of an examination order, which includes information about the sex and age of a patient, a body part to be imaged, and an examination purpose, and shows the examination order on a display. The examination order is inputted from an external system e.g. a HIS (hospital information system) or a RIS (radiography information system) for managing patient data and radiographic examination data, or inputted manually by the operator such as the radiological technician. The operator confirms the details of the examination order on the display, and inputs the imaging condition on an operation screen of the console 24 in accordance with the details of the examination order.

The console 24 sends the imaging condition to the imaging control unit 23, and also applies various types of image processes such as a gamma correction and a frequency process to X-ray image data sent from the imaging control unit 23. The X-ray image after being applied with the image processes is shown on the display of the console 24, and its data is stored to a data storage device including a hard disk and a memory of the console 24 and an image storage server connected to the console 24 through a network.

Figure 2:
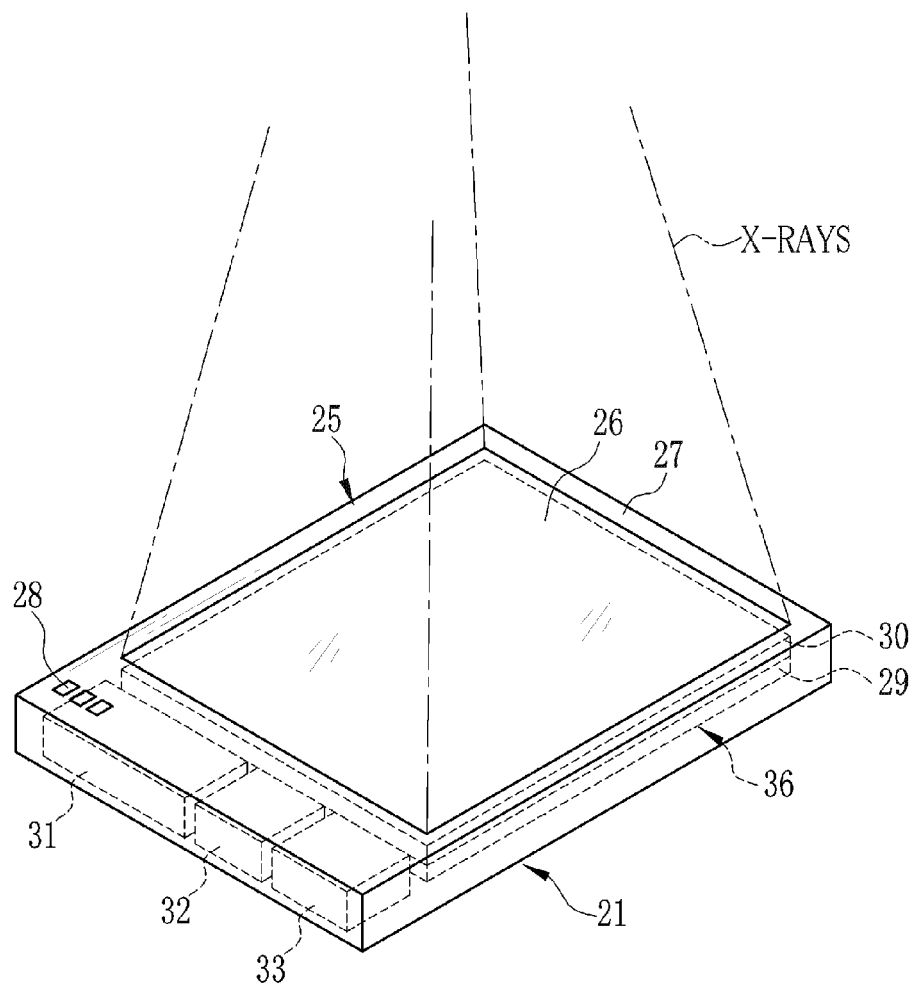
FIG. 2 is a perspective view showing the structure of an X-ray image detecting device.

As shown in FIG. 2, the X-ray image detecting device 21 is provided with a housing 25 in which a rectangular top surface becomes a radiation irradiation surface. The housing 25 is constituted of a top plate 26 having the irradiation surface, and a housing main body 27 composing a part of the housing 25 other than the top plate 26. For example, the top plate 26 is made of carbon or the like, and the housing main body 27 is made of metal, resin, or the like. Thus, it is possible to ensure the strength of the housing main body 27 while preventing X-ray absorption by the top plate 26.

The top surface of the housing 25 is provided with an indicator 28 being a notification section for notifying the radiological technician of operation states and the like of the X-ray image detecting device 21. The indicator 28 includes, for example, a plurality of light emitting elements, and combinations of emission of the light emitting elements indicate the operation states of the X-ray image detecting device 21, a remaining battery amount, and the like. As the operation states, there are "a ready state" being ready for radiography, "a data transmission state" being in the course of transmitting taken image data, and the like. A display device such as an LCD may be used as the indicator 28.

The FPD 36, being an image detector for detecting the X-ray image, is disposed in the housing 25 of the X-ray image detecting device 21 so as to be opposed to the irradiation surface. The FPD 36 is of an indirection conversion type, which has a scintillator 29 for converting the X-rays into visible light and a detection panel 30 for making a photoelectric conversion of the visible light converted by the scintillator 29. The FPD 36 adopts an irradiation side sampling (ISS) method in which the detection panel 30 is disposed on an X-ray irradiation side of the scintillator 29. Note that, the FPD 36 may adopt a penetration side sampling (PSS) method in which the disposition of the scintillator 29 and the detection panel 30 is reversed.

The housing 25 contains various electronic circuits 31, a battery 32, and a communicator 33 disposed at one end along a short direction of the irradiation surface. Various electronic circuits 31, being electronic circuitry for controlling the FPD 36, are protected with an X-ray shielding material in order to prevent damage to various electronic parts by X-ray application. The battery 32, which is installed in the housing 25 in a rechargeable and detachable manner, supplies an electric power to the FPD 36, the various electronic circuits 31, and the communicator 33. The communicator 33 makes a communication with the imaging control unit 23 in a wired or wireless method.

Figure 3:
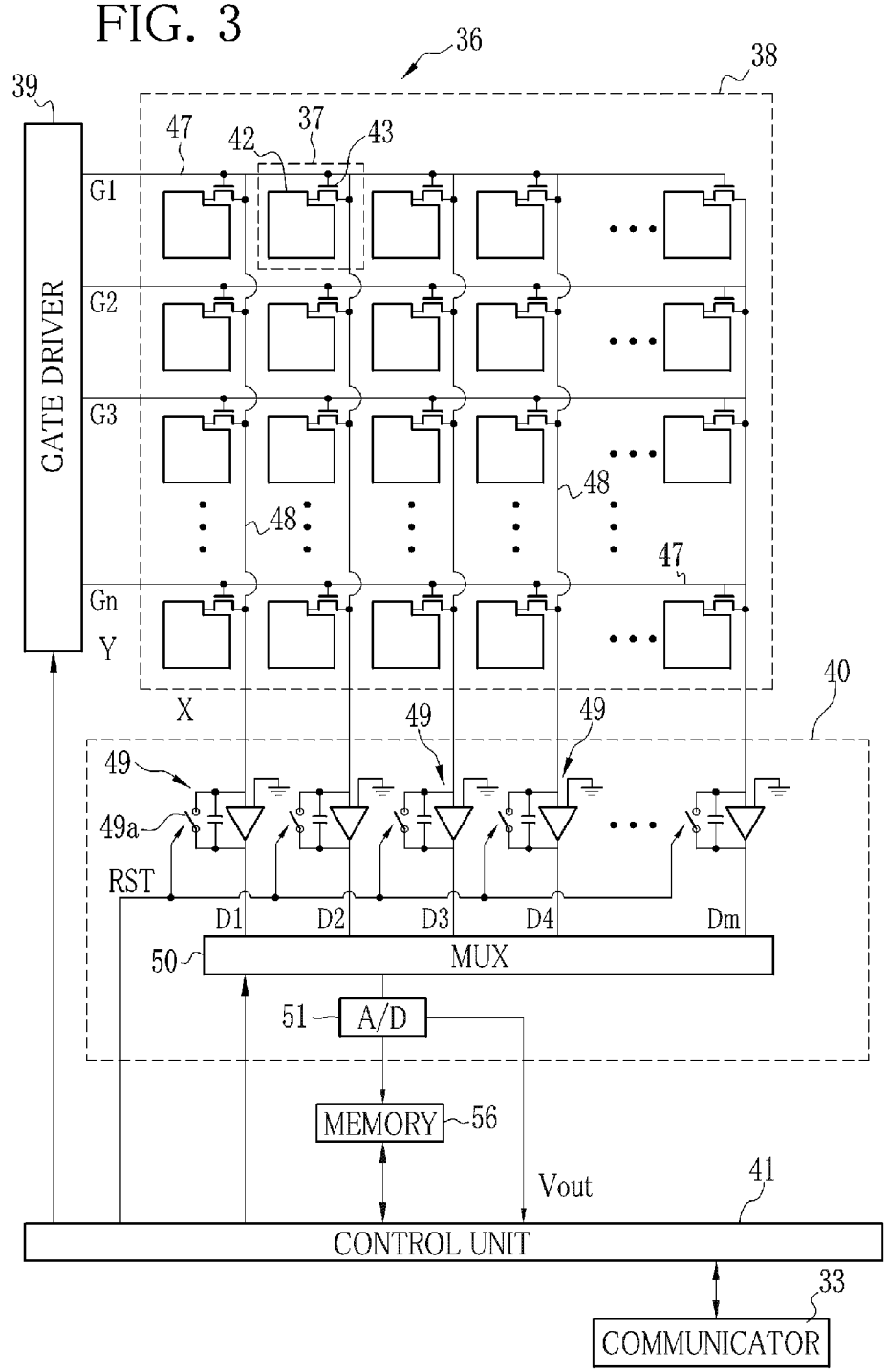
FIG. 3 is an explanatory view showing the structure of an FPD.

In FIG. 3, the FPD 36 is provided with the detection panel 30 having an imaging area 38, a gate driver 39 for controlling a readout of signal charge by driving pixels 37, a signal processing circuit 40 for converting the signal charge read from the pixels 37 into digital data and outputting the digital data, and a control unit 41 for controlling the gate driver 39 and the signal processing circuit 40 to control the operation of the FPD 36. The imaging area 38 has a TFT active matrix substrate and an arrangement of a plurality of pixels 37 on this substrate, and each pixel 37 accumulates signal charge in accordance with an X-ray irradiation amount. To the control unit 41, the communicator 33, which communicates with the imaging control unit 23 in a wired or wireless method, is connected. The plurality of pixels 37 are arranged in a two-dimensional matrix of n rows (X direction) and m columns (Y direction) at a predetermined pitch.

The FPD 36 is of the indirect conversion type, which has the scintillator 29 for converting the X-rays into the visible light and the pixels 37 for making a photoelectric conversion of the visible light converted by the scintillator 29. The scintillator 29 is disposed so as to be opposed to the entire surface of the imaging area 38 having the arrangement of the pixels 37. The scintillator 29 is made of a phosphor such as CsI (cesium iodide) or GOS (gadolinium oxysulfide). Note that, a direct conversion type FPD using a conversion layer (amorphous selenium or the like) for directly converting the X-rays into the electric charge may be used instead.

The pixel 37 is provided with a photodiode 42 being a photoelectric conversion element that produces the electric charge (electron and hole pairs) upon an entry of the visible light, a capacitor (not shown) for accumulating the electric charge produced by the photodiode 42, and a thin film transistor (TFT) 43 being a switching element.

The photodiode 42 has a semiconductor layer (of a PIN type, for example) such as a-Si (amorphous silicon), and upper and lower electrodes disposed on the top and bottom of the semiconductor layer. The lower electrode of the photodiode 42 is connected to the TFT 43. The upper electrode of the photodiode 42 is connected to a bias line (not shown).

A bias voltage is applied to the upper electrodes of the photodiodes 42 of all the pixels 37 in the imaging area 38 through the bias lines. The application of the bias voltage produces an electric field in the semiconductor layer of the photodiode 42. The electric charge (electron and hole pairs) produced in the semiconductor layer by the photoelectric conversion is attracted to the upper and lower electrodes, one of which has positive polarity and the other had negative polarity. Thereby, the electric charge is accumulated in the capacitor.

A gate electrode of the TFT 43 is connected to a scan line 47. A source electrode of the TFT 43 is connected to a signal line 48. A drain electrode of the TFT 43 is connected to the photodiode 42. The scan lines 47 and the signal lines 48 are routed into a lattice. The number of the scan lines 47 coincides with the number of the rows (n rows) of the pixels 37 in the imaging area 38, and each scan line 47 is a common line connected to a plurality of pixels 37 of one row. The number of the signal lines 48 coincides with the number of the columns (m columns) of the pixels 37, and each signal line 48 is a common line connected to a plurality of pixels 37 of one column. Every scan line 47 is connected to the gate driver 39, and every signal line 48 is connected to the signal processing circuit 40.

By driving the TFTs 43, the gate driver 39 makes the pixels 37 perform the accumulation operation for accumulating the signal charge in the pixels 37 in accordance with the X-ray irradiation amount, a readout operation for reading the signal charge from the pixels 37, and a reset operation for resetting the electric charge accumulated in the pixels 37. The control unit 41 controls start timing of each operation described above performed by the gate driver 39.

In the accumulation operation, while the TFT 43 is turned off, the signal charge is accumulated in the pixel 37. In the readout operation, the gate driver 39 sequentially issues gate pulses G1 to Gn, which drive the TFTs 43 of the same row at a time. Thus, the scan lines 47 are activated one by one, and the TFTs 43 connected to the activated scan line 47 are turned on from row to row.

Upon turning on the TFTs 43 of one row, the signal charge accumulated in each of the pixels 37 of one row is inputted to the signal processing circuit 40 through each signal line 48. The signal processing circuit 40 converts the signal charge of one row into voltages, and outputs the voltages corresponding to the signal charge of each pixel 37 as voltage signals D1 to Dm. The analog voltage signals D1 to Dm are converted into digital data, and image data, which includes digital pixel values representing density in each of the pixels of one row, is produced. The image data is outputted to a memory 56 contained in the housing of the X-ray image detecting device 21.

A dark current occurs in the semiconductor layer of the photodiode 42 regardless of the presence or absence of an incidence of the X-rays. Dark charge, being electric charge corresponding to the dark current, is accumulated in the capacitor due to the application of the bias voltage. The dark charge becomes a noise component of the image data, so the reset operation is performed to remove the dark charge. The reset operation is an operation for discharging the dark charge that has occurred in the pixel 37 from the pixel 37 through the signal line 48.

The reset operation adopts, for example, a sequential reset method in which the pixels 37 are reset on a row-by-row basis. In the sequential reset method, the gate pulses G1 to Gn are sequentially issued from the gate driver 39 to the scan lines 47, so that the TFTs 43 of the pixels 37 are turned on from row to row. While the TFT 43 is turned on, the dark charge is inputted from the pixel 37 to the signal processing circuit 40 through the signal line 48.

In the reset operation, the signal processing circuit 40 does not read output voltages in accordance with the dark charge, in contrast to the readout operation. In the reset operation, a reset pulses RST is outputted from the control unit 41 to the signal processing circuit 40 in synchronization with the issue of each of the gate pulses G1 to Gn. Upon inputting the reset pulses RST to the signal processing circuit 40, reset switches 49a of integration amplifiers 49, which will be described later, are turned on, so the inputted dark charge is reset.

Instead of the sequential reset method, a parallel reset method or all pixels reset method may be used, In the parallel reset method, a plurality of rows of pixels are grouped together, and sequential reset is performed in each group so as to concurrently discharge the dark charge from the rows of the number of the groups. In the all pixels reset method, the gate pulse is inputted to every row to discharge the dark charge from every pixel at a time. Adopting the parallel reset method and the all pixels reset method allows speeding up the reset operation.

The signal processing circuit 40 includes the integration amplifiers 49, a multiplexer (MUX) 50, an A/D converter 51, and the like. The integration amplifier 49 is connected to each signal line 48 on a one-by-one basis. The integration amplifier 49 is composed of an operational amplifier and a capacitor connected between input and output terminals of the operational amplifier. The signal line 48 is connected to one of the input terminals of the operational amplifier. The other input terminal (not shown) of the integration amplifier 49 is connected to ground (GND). The integration amplifiers 49 convert the signal charge inputted from the signal lines 48 into voltage signals D1 to Dm by integration, and output the voltage signals D1 to Dm.

The output terminal of the integration amplifier 49 of each column is connected to the MUX 50 through another amplifier (not shown) for amplifying the voltage signal D1 to Dm and a sample holder (not shown) for holding the voltage signal D1 to Dm. The MUX 50 selects in turn one of the integration amplifiers 49 connected in parallel, and inputs the voltage signals D1 to Dm outputted from the selected integration amplifiers 49 in series to the A/D converter 51. The A/D converter 51 converts the analog voltage signals D1 to Dm into digital pixel values in accordance with each signal level.

In the readout operation for reading out the signal charge after the accumulation operation, the TFTs 43 are turned on by the gate pulses on a row-by-row basis. In the row turned on, the signal charge accumulated in the capacitor of the pixel 37 is inputted to the integration amplifier 49 of each column through the signal line 48.

Upon outputting the voltage signals D1 to Dm of one row from the integration amplifiers 49, the control unit 41 outputs the reset pulse (reset signal) RST to the integration amplifiers 49 to turn on the reset switches 49a of the integration amplifiers 49. Thus, the signal charge of one row accumulated in the integration amplifiers 49 is reset. Upon resetting the integration amplifiers 49, the gate driver 39 outputs the gate pulse of the next row, to start reading the signal charge from the pixels 37 of the next row. These steps are sequentially repeated to read the signal charge from the pixels 37 of every row.

Upon completing the readout from every row, image data representing an X-ray image of one screen is recorded to the memory 56. To the image data recorded in the memory 56, an image correction process is applied, which includes an offset correction for removing an offset component being fixed pattern noise caused by an individual difference and environment of the FPD 36, a sensitivity correction for correcting sensitivity variations among the photodiodes 42 of the pixels 37, variations in output characteristics of the signal processing circuit 40, and the like. The image data is read from the memory 56 to the imaging control unit 23, and sent to the console 24. Thereby, the X-ray image of the examinee H is detected.

Figure 4:
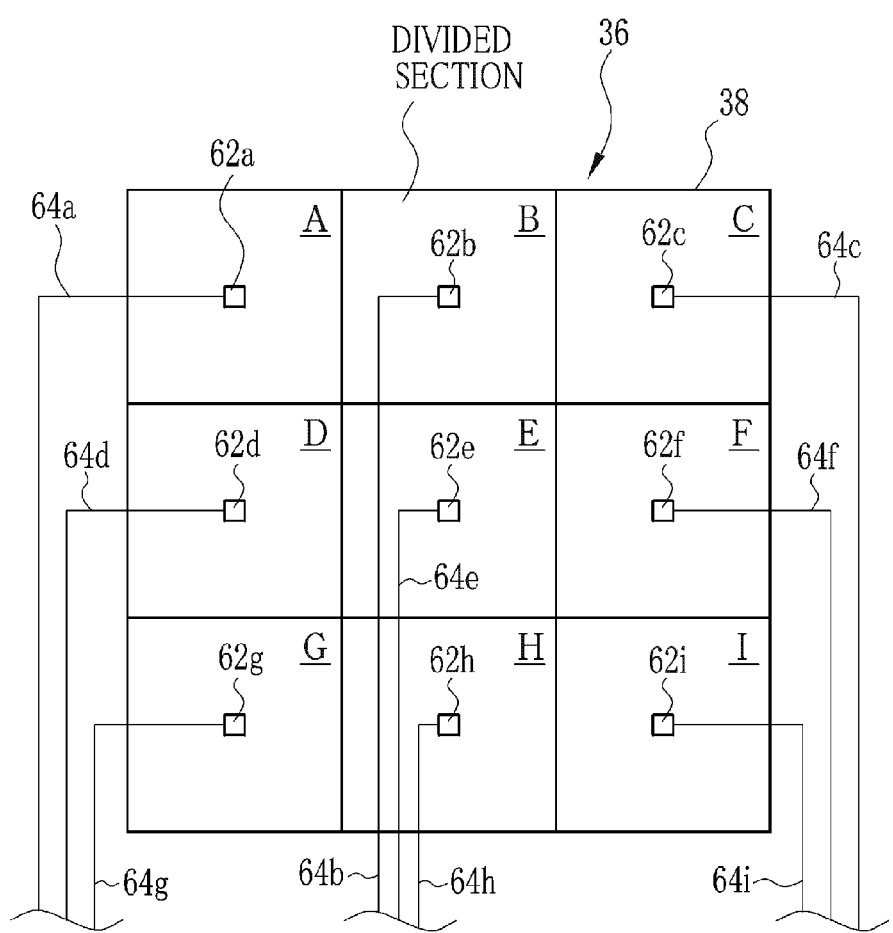
FIG. 4 is an explanatory view showing the structure of divided sections.

As shown in FIG. 4, the imaging area 38 of the FPD 36 is partitioned into a plurality of divided sections, for example, divided sections A to I of two-dimensional three rows (X direction) and three columns (Y direction). Each of the divided sections A to I has at least one short pixel 62a to 62i, which corresponds to a radiation detector of this invention. Note that, the number of the divided sections may be more or less than nine. Furthermore, a plurality of short pixels may be provided in each divided section, and the number of the short pixels disposed in each divided section is preferably the same for the purpose of equalizing the sensitivity of every divided section.

Figure 5:
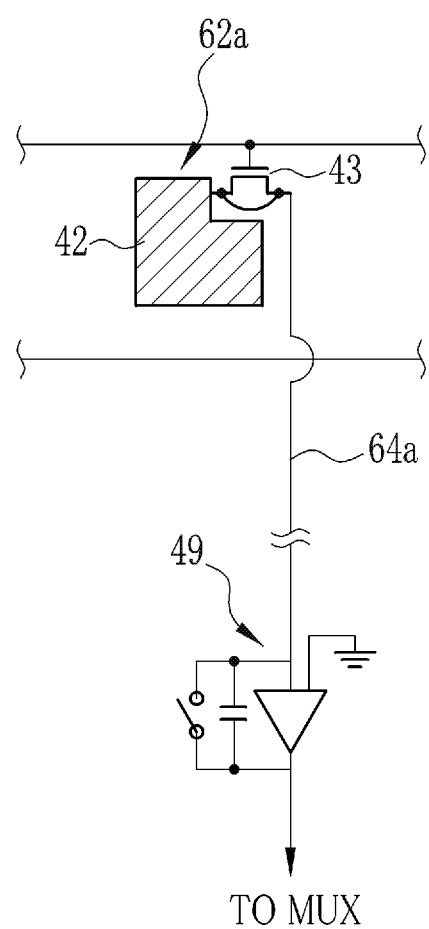
FIG. 5 is an explanatory view showing the structure of a short pixel.

As shown in FIG. 5, the short pixel 62a has almost the same structure as the pixel 37. The short pixel 62a has the photodiode 42 and the TFT 43. The photodiode 42 produces the signal charge in accordance with the X-ray irradiation amount. However, in contrast to the pixel 37 in which the TFT 43 switches on and off the electrical connection to the signal line 48, the short pixel 62a does not have a switching function by a short between a source and a drain of the TFT 43, and is connected to a specific signal line 64a to which neither the pixel 37 nor the short pixel of another divided section is connected. Thus, the signal charge produced in the photodiode 42 of the short pixel 62a always flows through the specific signal line 64a into the integration amplifier 49. Note that, instead of coupling the source and the drain of the TFT 43 of the short pixel 62a, the photodiode 42 may be directly connected to the specific signal line 64a without providing the TFT 43 itself in the short pixel 62a. The short pixels 62b to 62i of the other divided sections have the same structure as the short pixel 62a, so detailed description thereof will be omitted.

The control unit 41 measures the X-ray irradiation amount applied from the X-ray source 13 to the FPD 36 based on an output of each of the short pixels 62a to 62i. The X-ray irradiation amount is an irradiation amount per unit of time, and also called X-ray intensity. The control unit 41 selects by the MUX 50 the integration amplifiers 49 to which the signal charge from the short pixels 62a to 62i is inputted, and reads the voltage signals of the integration amplifiers 49 as output voltages Vout (detection signals) of the short pixels 62a to 62i. The output voltage Vout corresponds to the X-ray irradiation amount per unit of time. Upon reading the output voltages Vout one time, the control unit 41 resets the integration amplifiers 49. During the accumulation operation, the control unit 41 repeats the step of reading the output voltages Vout at extremely short intervals with respect to the X-ray emission time, so as to monitor variations in the X-ray irradiation amount during the X-ray emission.

The control unit 41 converts values of the output voltages Vout into digital data, and records the digital data to the memory 56. The control unit 41 monitors variations in the X-ray irradiation amount applied from the X-ray source 13 based on variations in the output voltages Vout stored in the memory 56, to detect the start of X-ray emission.

The control unit 41 can measure the total X-ray irradiation amount applied from the X-ray source 13 to the FPD 36 based on the outputs of the short pixels 62a to 62i. The control unit 41 reads the output voltages Vout of the short pixels 62a to 62i at the short intervals after the start of X-ray emission, as in the case of detecting the start of X-ray emission as described above, and measures the total X-ray irradiation amount by integrating the values of the output voltage Vout.

The control unit 41 detects the start of X-ray emission using the short pixels 62a to 62i, and performs a synchronization control, i.e. starting the accumulation operation of the FPD 36 in synchronization with the start of X-ray emission. After that, the control unit 41 performs an automatic exposure control, i.e. stopping the X-ray emission from the X-ray source 13 based on the total X-ray irradiation amount measured by the short pixel 62a to 62i.

As described above, the control unit 41 performs both the synchronization control and the automatic exposure control on the basis of the output voltage Vout of the short pixel 62. However, the size of an area (first detection area) used for detecting the start of X-ray emission in the synchronization control is different from the size of a section (second detection area) used for measuring the total X-ray irradiation amount in the automatic exposure control. To be more specific, all of the divided sections A to I corresponding to the entire imaging area 38 of the FPD 36 are used as the first detection area in the synchronization control, while only part of the divided sections A to I is used as the second detection area in the automatic exposure control. In other words, a part of the first detection area used in the synchronization control is used as the second detection area in the automatic exposure control. Thus, the size of the first detection area is larger than that of the second detection area, and the size of the second detection area is smaller than that of the first detection area.

Figure 6:
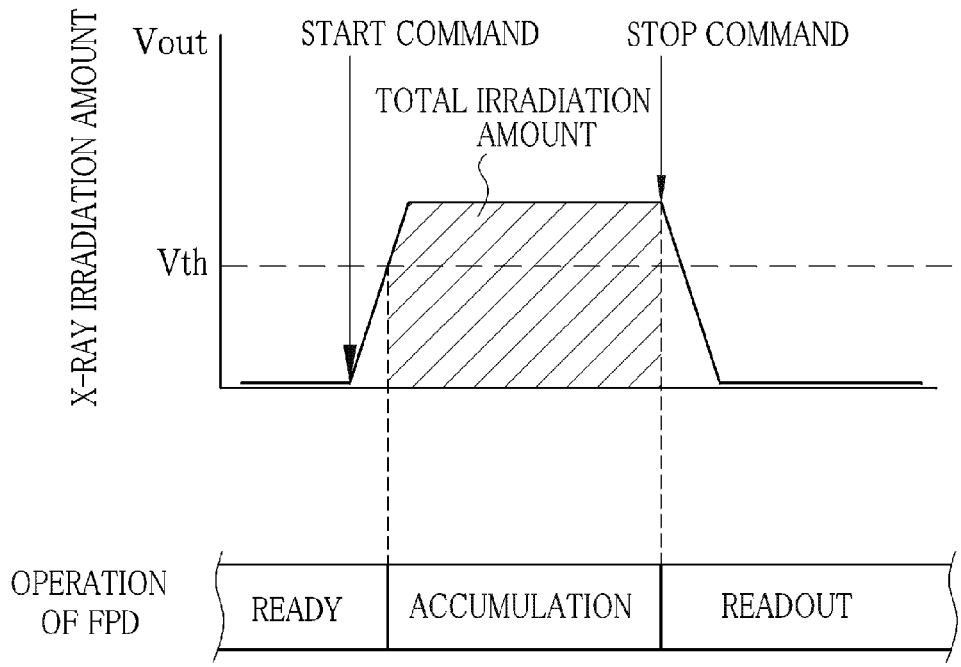
FIG. 6 is an explanatory view showing a synchronous control procedure according to a first embodiment.

FIG. 6 shows an X-ray irradiation amount and an operation state of the FPD 36 controlled based on the irradiation amount. The X-ray irradiation amount takes an approximately trapezoidal shape in a graph in which a horizontal axis represents time and a vertical axis represents the X-ray irradiation amount (output voltage Vout). When the X-ray source 13 starts the X-ray emission upon receiving a start command, the X-ray irradiation amount gradually increases to a peak value, which depends on the tube current set as the imaging condition. The X-ray irradiation amount is kept almost constant in the vicinity of the peak value, until receiving a stop command. After the X-ray source 13 stops the X-ray emission upon receiving the stop command, the X-ray irradiation amount gradually decreases to zero, and the X-ray emission is completely stopped.

The control unit 41 sets a threshold value of the total X-ray irradiation amount on the basis of the examination order inputted from the console 24, including the sex and age of the patient, the body part to be imaged, the examination purpose, and the like. In response to a preparation command from the imaging control unit 23, the control unit 41 shifts the FPD 36 to the ready state. In the ready state, the control unit 41 makes the FPD 36 perform the reset operation.

In the ready state, the control unit 41 detects the start of X-ray emission from the X-ray source 13 by using all the divided sections A to I. To be more specific, the control unit 41 determines, out of the short pixels 62a to 62i, a divided section whose output voltage Vout corresponding to the signal charge is the largest. The X-ray irradiation amount is measured based on the output voltage Vout of the determined divided section, and variations in the X-ray irradiation amount is started to be monitored. The control unit 41 compares the output voltage Vout of the short pixel of the determined divided section with a predetermined threshold value Vth. When the output voltage Vout exceeds the threshold value Vth, the start of X-ray emission is detected.

Figure 7:
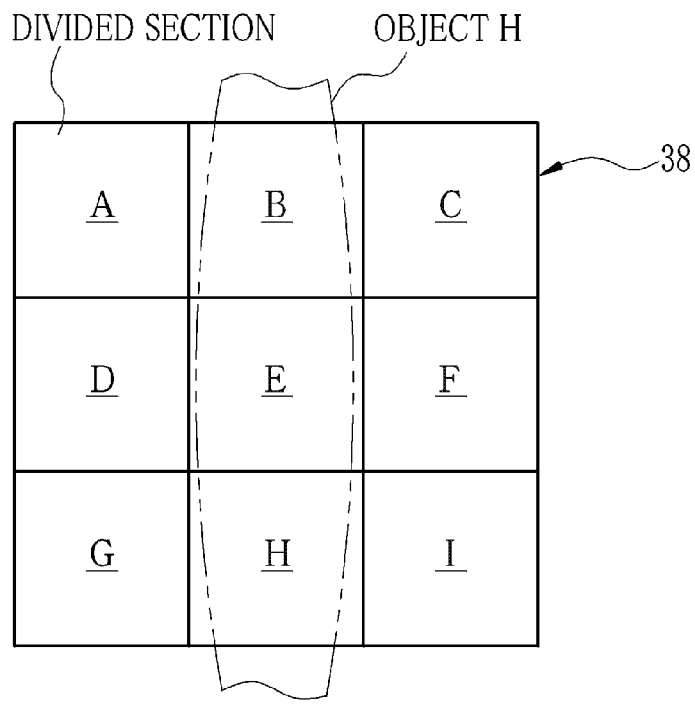
FIG. 7 is an explanatory view showing an example of disposition of an object with respect to an imaging area.
Figure 8:
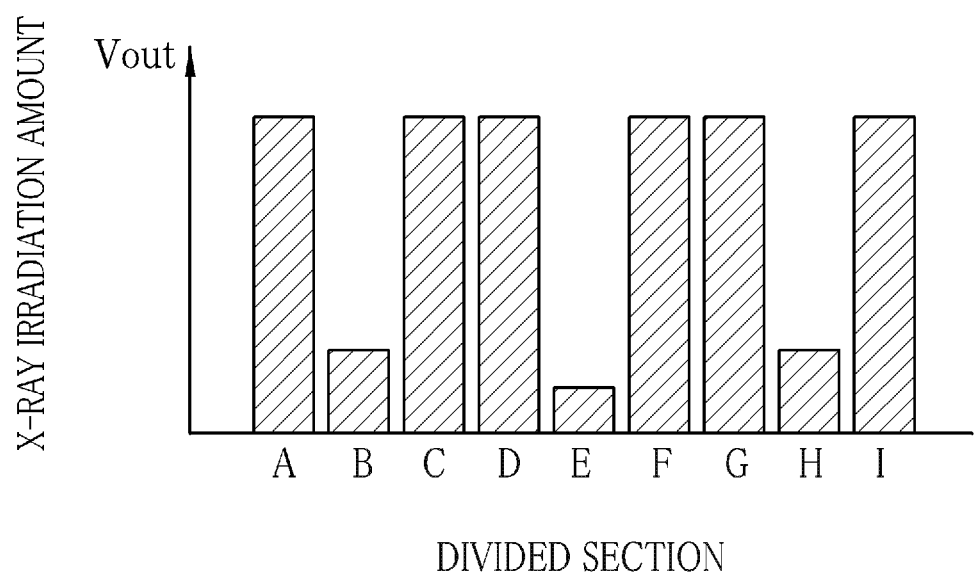
FIG. 8 is a graph showing a detection signal of the short pixel of each divided section.

In FIG. 7, when the object H is small relative to the size of the imaging area 38, for example, when the object H is a hand or a foot, the object H is positioned approximately in the middle of the imaging area 38 so as to be opposed to the divided sections B, E, and H of the imaging area 38. FIG. 8 is a graph showing the output voltages Vout of the short pixels 62a to 62i disposed in the divided sections A to I, respectively. According to this graph, since the divided sections A, C, D, F, G, and I that are not opposed to the object correspond to the directly exposed area, the output voltages Vout of the divided sections A, C, D, F, G, and I are higher than those of the divided sections B, E, and H opposed to the object H.

In the synchronization control, all the divided sections A to I are used as the first detection area, the control unit 41 monitors all the output voltages Vout of the short pixels 62a to 62i of the divided areas A to I. At the time when any of the output voltages Vout of the short pixels 62a to 62i has reached the threshold value, it is judged that the X-ray emission has been started and the start of X-ray emission is detected. In an example of FIGS. 7 and 8, the output voltages Vout of the short pixels existing in the divided sections A, C, D, F, G, and I corresponding to the directly exposed area reach the threshold value earlier than those of the short pixels existing in the divided sections B, E, and H opposed to the object H. By designating all the divided sections A to I as the first detection area for use in the synchronization control, it is possible to use the directly exposed area of the FPD 36 for detecting the start of X-ray emission. Accordingly, the start of X-ray emission can be detected with high accuracy.

Upon detecting the start of X-ray emission, the control unit 41 turns off the TFTs 43 of the pixels 37 to shift the FPD 36 from the ready state to the accumulation operation. Since the TFTs 43 are turned off, the pixels 37 accumulate the signal charge in accordance with the X-ray irradiation amount.

Even of the TFTs 43 of the pixels 37 are turned off, the short pixels 62a to 62i are always short to the specific signal lines 64a to 64i. After the FPD 36 is shifted to the accumulation operation upon the start of X-ray emission, the control unit 41 starts the automatic exposure control in which the X-ray irradiation amount is measured based on the output of the short pixel 62a to 62i flowing into the specific signal line 64a to 64i.

The control unit 41 determines the second detection area to be used in the automatic exposure control, out of the divided sections A to I composing the first detection area. As shown in FIGS. 7 and 8, the divided sections A, C, D, F, G, and I compose the directly exposed area, out of the divided sections A to I. Since the X-ray irradiation amount is large in the directly exposed area, performing the automatic exposure control based on the output voltage Vout of the short pixel existing in the directly exposed area may cause underexposure. Thus, to appropriately perform the automatic exposure control, the divided sections B, E, and H opposed to the object H are preferably used. The control unit 41 determines the divided sections B, E, and H having the short pixels 62b, 62e, and 62h, which have relatively low output voltages Vout, based on the output voltages Vout of the short pixels 62a to 62i of the divided sections A to I. The determined divided sections B, E, and H are chosen as the second detection area.

In such a second detection area determining process, for example, the output voltages Vout of the short pixels 62a to 62i corresponding to all the divided sections A to I may be read in the automatic exposure control. However, the output voltages Vout of the short pixels 62a to 62i have already been read in the synchronization control before the automatic exposure control, so the second detection area determining process may be performed using the output voltages Vout read in the synchronization control. Using the output voltages Vout read in the synchronization control eliminates the need for newly reading the output voltages Vout in the second detection area determining process and shortens processing time.

In the automatic exposure control, the control unit 41 measures the total X-ray irradiation amount by integrating a signal value corresponding to the output voltage Vout of each of the short pixels 62b, 62e, and 62h of the divided sections B, E, and H determined as the second detection area, and compares the measurement result with a threshold value. When the total X-ray irradiation amount has reached the threshold value, the control unit 41 transmits the stop signal to the source control unit 14 through the imaging control unit 23. Upon receiving the stop signal, source control unit 14 issues the stop command to the X-ray source 13 to stop the X-ray emission. Concurrently with the transmission of the stop signal, the control unit 41 ends the accumulation operation of the FPD 36 and starts the readout operation.

The automatic exposure control is performed using only the short pixels 62b, 62e, and 62h of the divided sections B, E, and H opposed to the object H, which exclude the directly exposed area, so that the accuracy of the automatic exposure control is increased.

Figure 9:
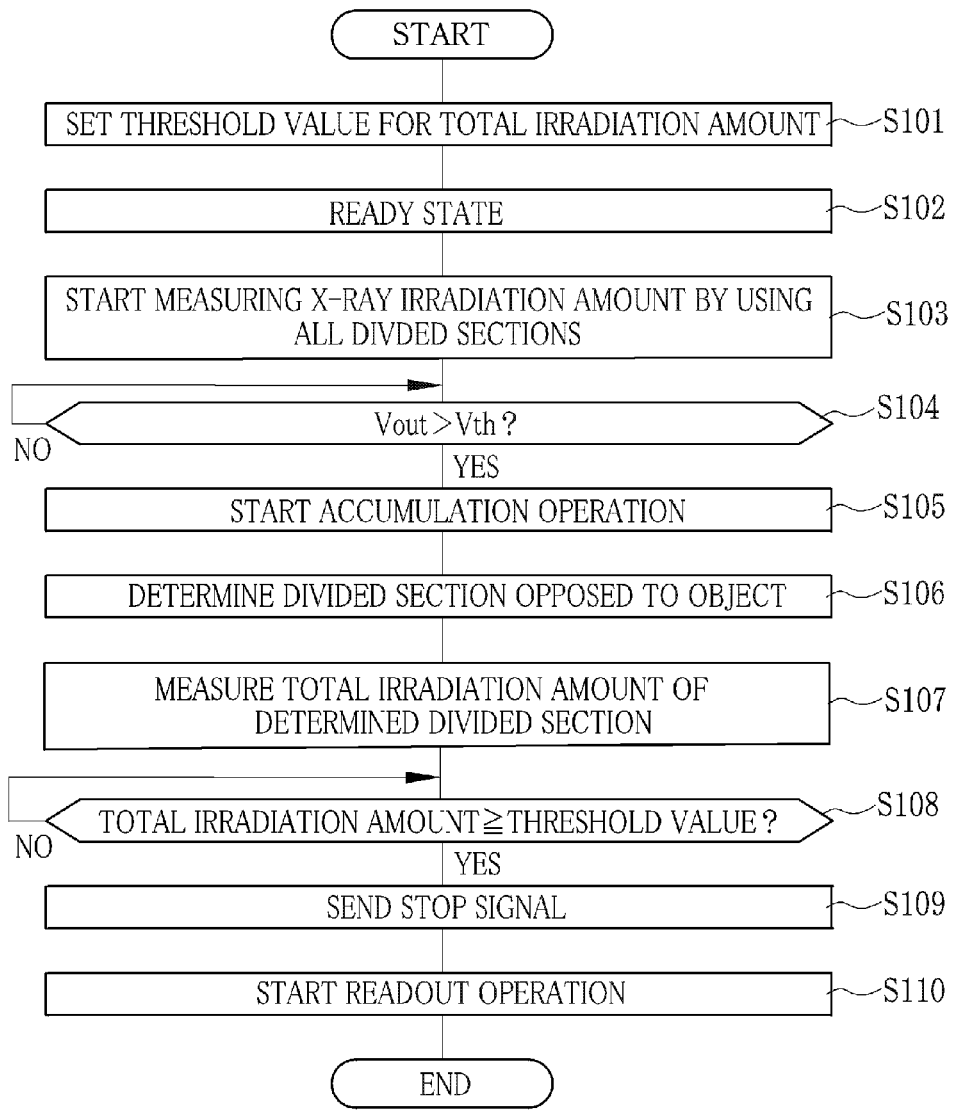
FIG. 9 is a flowchart of an FPD control procedure according to the first embodiment.

The operation of the X-ray image detecting device 21 installed in the X-ray image capturing system 10 of FIG. 1 will be described with referring to a flowchart of FIG. 9. The body part of the examinee H to be imaged and the irradiation field of the X-ray source 13 are positioned with respect to the imaging support 22, which is loaded with the X-ray image detecting device 21. The imaging condition including the tube voltage, the tube current, the emission time, and the like are set to the X-ray source 13. To the imaging control unit 23, the examination order including the sex and the age of the patient, the body part to be imaged, the examination purpose, and the like is inputted from the console 24. The control unit 41 of the X-ray image detecting device 21 sets the threshold value for the total X-ray irradiation amount on the basis of the examination order (S101).

Upon inputting the preparation command from the imaging control unit 23 to the control unit 41 of the X-ray image detecting device 21, the FPD 36 is shifted to the ready state (S102). Upon inputting the emission start command to the X-ray source 13 by a press of the emission switch 15, the X-ray source 13 starts emitting the X-rays to the examinee H. The control unit 41 performs the synchronization control using all the divided sections A to I of the FPD 36 as the first detection area. The control unit 41 monitors variations in the X-ray irradiation amount based on the output voltage Vout of the short pixel 62a to 62i existing in each of the divided sections A to I (S103). When the X-ray irradiation amount is increased and any of the output voltages Vout of the short pixels 62a to 62i exceeds the threshold value Vth, the start of X-ray emission is detected (S104). Upon detecting the start of X-ray emission, the control unit 41 turns off the TFTs 43 of the pixels 37 and starts the accumulation operation (S105).

The control unit 41 determines the divided sections B, E, and H that are opposed to the object H, on the basis of the output voltages Vout of the short pixels 62a to 62i read in the synchronization control (S106). The control unit 41 uses the determined divided sections B, E, and H as the second detection area in the automatic exposure control. The control unit 41 measures the total X-ray irradiation amount by integrating the output voltage Vout of the short pixel 62b, 62e, and 62h of the determined divided section B, E, and H (S107), and compares the total X-ray irradiation amount with the threshold value (S108). When the total X-ray irradiation amount has reached the threshold value, the control unit 41 transmits the stop signal to the source control unit 14 through the imaging control unit 23 (S109). Upon receiving the stop signal, the source control unit 14 transmits the stop command to the X-ray source 13 to stop the X-ray emission. The control unit 41 ends the accumulation operation of the FPD 36 in synchronization with the transmission of the stop signal, and shifts the FPD 36 to the readout operation (S110). The read X-ray image is recorded to the memory 56 and transmitted to the console 24.

According to this embodiment, as described above, in the synchronization control, all the divided sections A to I including the directly exposed area are determined as the first detection area, and the output voltages Vout of the short pixels 62a to 62i existing in the first detection area are monitored. As a result, it is possible to detect the start of X-ray emission based on the output voltage Vout of the short pixel existing in the directly exposed area. The use of the directly exposed area results in detecting the start of X-ray emission with high accuracy. In the automatic exposure control, out of the first detection area, the divided section that is opposed to the object is used as the second detection area for measuring the total X-ray irradiation amount. Thus, the automatic exposure control is performed appropriately based on the total X-ray irradiation amount applied to the object, and hence it is possible to carry out the automatic exposure control with high accuracy.

The X-ray irradiation amount is measured using the short pixel 62a to 62i provided in the imaging area 38. Since the short pixel 62a to 62i has almost the same structure and sensitivity to the X-rays as the normal pixel 37, the X-ray irradiation amount can be measured correctly. Also, it is possible to detect the start and stop of X-ray emission and measure the total X-ray irradiation amount with high accuracy. Almost the same structure facilitates manufacturing and minimizes increase in a manufacturing cost.

In this embodiment, the output voltages Vout of the short pixels 62a to 62i that are read in the synchronization control are used in the process of determining the second detection area for use in the automatic exposure control. Therefore, the automatic exposure control can be quickly carried out, as compared with the case of newly reading the output voltages Vout in the automatic exposure control.

In this embodiment, all the divided sections A to I existing in the imaging area 38 are chosen and the entire imaging area 38 is used as the first detection area in the synchronization control. When the object H is smaller than the imaging area 38 in size, the directly exposed area exists in the imaging area 38. Thus, by setting the entire imaging area 38 as the first detection area, the first detection area certainly includes the directly exposed area. Since the synchronization control is preferably performed based on a detection signal of the directly exposed area, assigning the entire imaging area 38 as the first detection area allows certainly performing the synchronization control with high accuracy.

However, the first detection area is not necessarily the entire imaging area 38, and, for example, may be part of the divided sections A to I. This is because even if a peripheral part of the imaging area 38 is excluded from the first detection area, the first detection area includes the directly exposed area in most cases. In the case of designating an area excluding the periphery of the imaging area 38 as the first detection area, for example, the number of division is increased from nine to sixteen (4×4), twenty-five (5×5), thirty-six (6×6), or the like and the size of each divided section is reduced, and an area excluding peripheral divided sections is designated as the first detection area.

In this embodiment, the second detection area determining process is performed based on the output voltages Vout read from the short pixels in the first detection area. However, for example, the second detection area to be used in the automatic exposure control may be automatically chosen in accordance with the details of the examination order or may be freely designated by a user. The position of the object disposed in the imaging area 38 depends on the body part to be imaged and the like to some extent, so the second detection area can be estimated without detecting the position of the object in the synchronization control.

A part of the first detection area is designated as the second detection area in this embodiment, but all or a part of the second detection area may not overlap with the first detection area in such a case that the second detection area is chosen in accordance with the details of the examination order or designated by the user. The relatively larger the first detection area, the likelier it becomes that the first detection area includes the directly exposed area.

In this embodiment, the start of X-ray emission is detected in the synchronization control by comparing the output voltage Vout of the short pixel of every divided section with the threshold value. However, the start of X-ray emission may be detected by addition of the output voltages Vout of the short pixels of a plurality of divided sections. This method provides the same effect as increase in the detection sensitivity of the short pixels, and hence improves the accuracy of the synchronization control.

(Second Embodiment)

Figure 10:
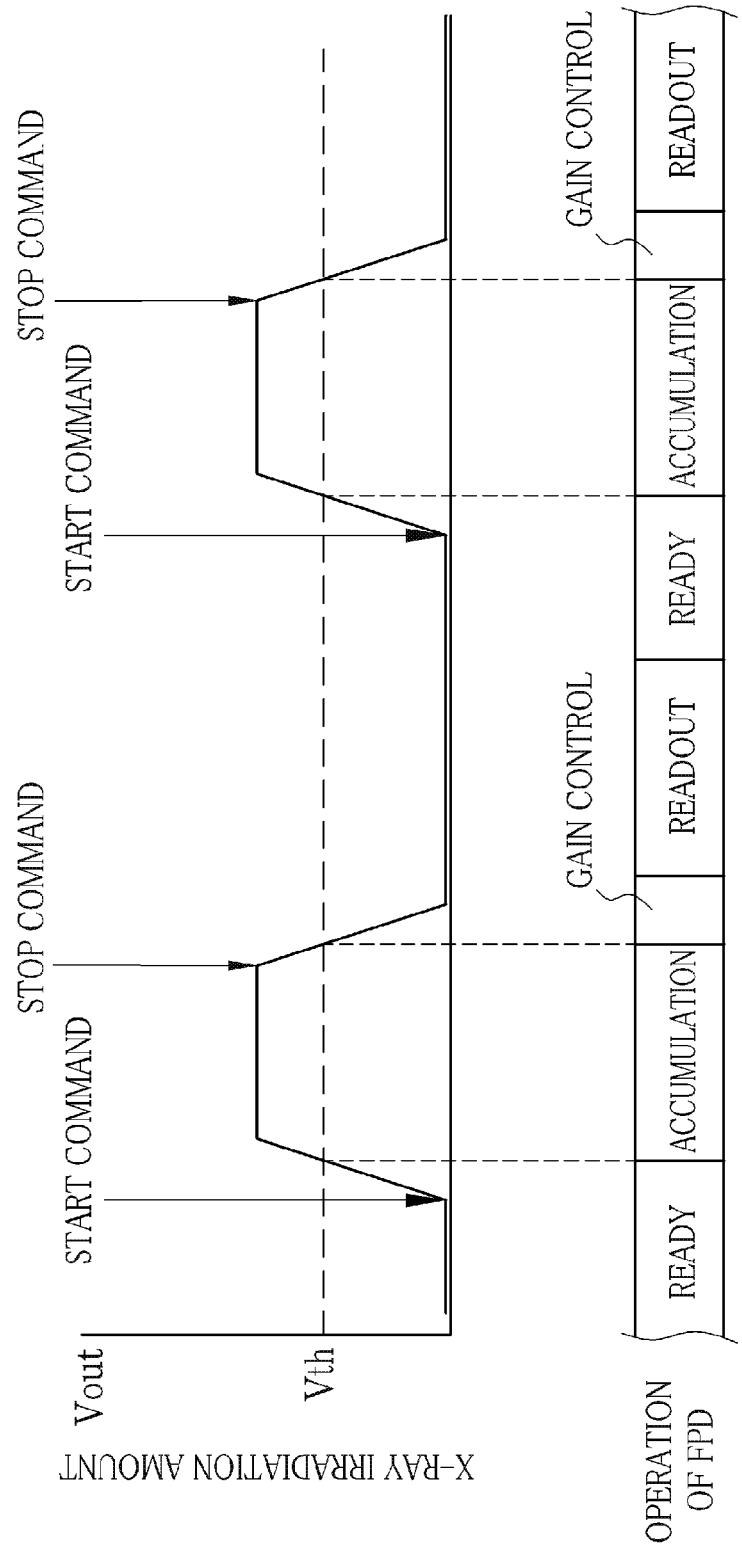
FIG. 10 is an explanatory view of an FPD control procedure according to a second embodiment.

The first embodiment is described with taking the capture of a still image as an example, but the present invention is applicable to the case of capturing a moving image, such as fluoroscopy. In capturing the moving image, as shown in FIG. 10, for example, the X-rays are continuously applied in pulses and one frame, which is an image composing part of the moving image, is obtained from each X-ray pulse. In this case, all the divided sections A to I are used as the first detection area in the synchronization control. The start of emission of each of the X-ray pulses applied continuously is detected based on the output voltages Vout of the short pixels 62a to 62i in the first detection area. In synchronization with the start of emission, the FPD 36 is shifted from the ready state to the accumulation operation. After that, the automatic exposure control is performed during the application of each X-ray pulse. In the automatic exposure control, the divided section that is opposed to the object is used as the second detection area. The total X-ray irradiation amount is measured on a pulse-by-pulse basis in accordance with the output voltage Vout of the short pixel in the second detection area. When the total X-ray irradiation amount has reached the threshold value, the X-ray emission from the X-ray source 13 is stopped, and the FPD 36 is shifted from the accumulation operation to the readout operation.

Note that, if the stop of X-ray emission from the X-ray source 13 cannot be controlled from the side of the FPD 36, only an operation of shifting the FPD 36 from the accumulation operation to the readout operation may be performed without performing transmission of the stop signal to the X-ray source 13.

The control unit 41 may measure the X-ray irradiation amount by one X-ray pulse in an accumulation period based on the output voltage Vout of the short pixel 62 of the second detection area, and control a gain of an amplifier in the readout operation based on the measurement result. The gain control can be performed by, for example, the integration amplifiers 49, amplifiers (not shown) connected to the output terminals of the integration amplifiers 49 for amplification of the voltage signals D1 to Dm, or the like. Since the plurality of short pixels 62 are disposed dispersively in the second detection area, the contrast of an X-ray image may be estimated based on outputs of the plurality of short pixels 62 disposed in different places, and the gain may be controlled based on the estimated contrast. Note that, such a gain control may be performed in obtaining the still image.

(Third Embodiment)

Figure 11:
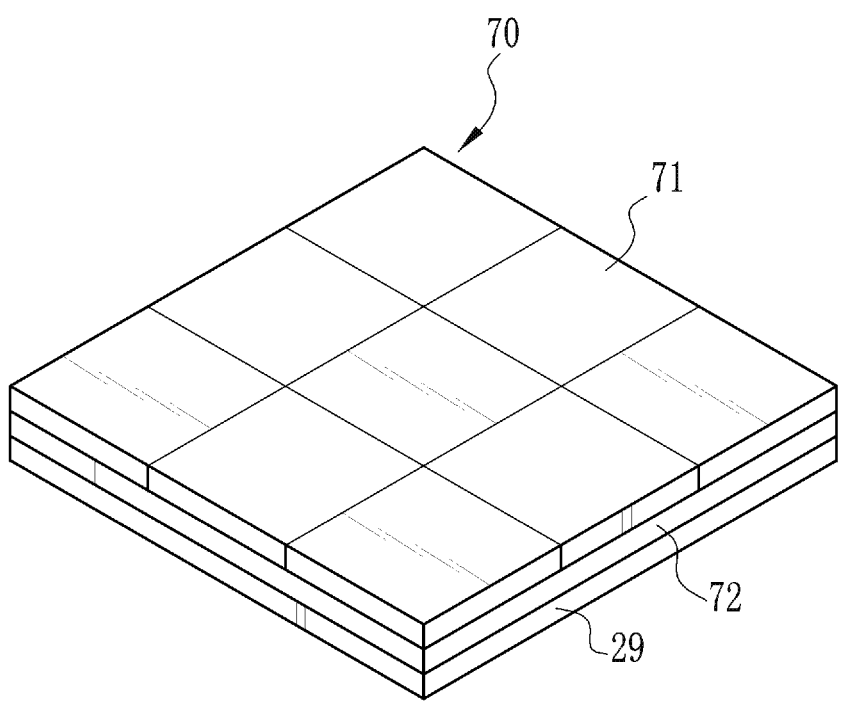
FIG. 11 is a perspective view showing the structure of an FPD according to a third embodiment.
Figure 12:
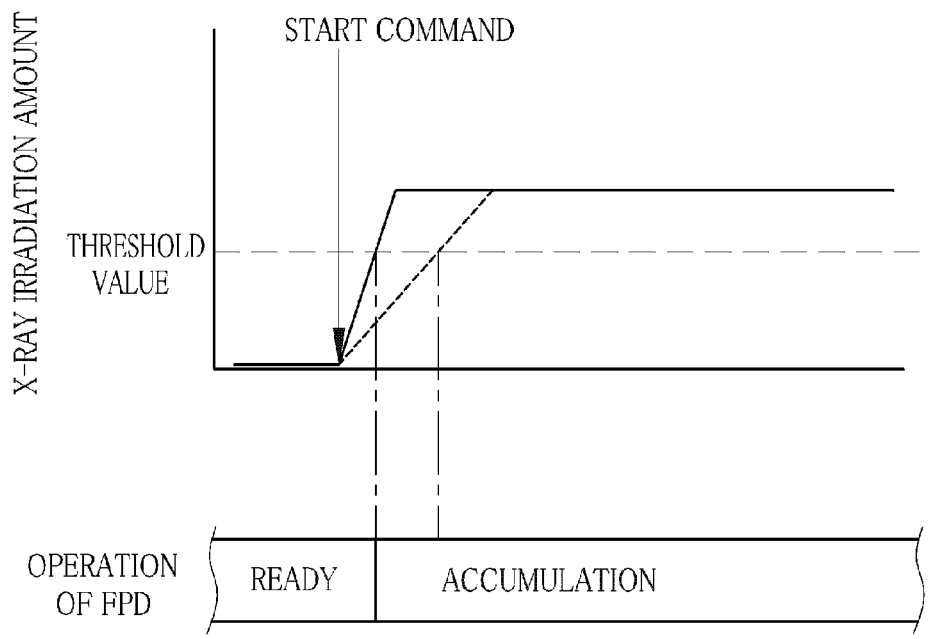
FIG. 12 is an explanatory view that compares detection of the start of X-ray emission between using X-rays applied to a directly exposed area and using X-rays passed through an object.

The short pixels are used as the radiation detectors in each of the above embodiments, but a plurality of photosensor arrays 71, each having a plurality of photodiodes arranged in a matrix, may be used instead of the short pixels as shown in an FPD 70 of FIG. 11. The photosensor array 71 is stacked on a detection panel 72, which is similar to the detection panel 30 of the first embodiment. The detection panel 72 is different from the detection panel 30 in terms of providing no short pixel, but the other structure thereof is the same as that of the detection panel 30. The photosensor array 71 is preferably made of OPC (organic photoelectric conversion material), for example. The OPC can be formed extremely thin and hardly absorbs the X-rays. Therefore, there is a merit that if the OPC is disposed on an X-ray irradiation side relative to the imaging area in the detection panel 72, the disposition of the OPC hardly affects X-ray image quality.

The radiation detectors exist in a wide variety of forms, other than the short pixels and the photosensor arrays. For example, the photodiode composing the pixel is applied with the bias voltage, and the bias current flowing through the bias line varies depending on the amount of the signal charge produced in the photodiode. The bias current may be detected to measure the X-ray irradiation amount. Furthermore, a leak current flows through the signal line in accordance with the amount of the signal charge produced in the photodiode, even while the TFT of the pixel is turned off. The leak current may be detected to measure the X-ray irradiation amount. In the method of detecting the bias current or the leak current, an element for detecting each current corresponds to the radiation detector.

The TFT type FPD, which has the TFT matrix substrate formed of a glass substrate, is described as an example, but an FPD having a CMOS image sensor or a CCD image sensor formed of a semiconductor substrate may be used instead. The use of the CMOS image sensor has the following merit. The CMOS image sensor can perform so-called nondestructive readout in which signal charge accumulated in a pixel can be read as a voltage signal through an amplifier provided in each pixel without flowing out to a signal line specific to readout. Accordingly, the X-ray irradiation amount can be measured even during the accumulation operation, by choosing an arbitrary pixel in the imaging area and reading signal charge from the pixel. Therefore, in the case of using the CMOS image sensor, any of normal pixels doubles as the radiation detector for use in measurement of the X-ray irradiation amount, without the need for providing another specific radiation detector.

Furthermore, as a matter of course, the X-ray image detecting device according to the present invention can take a wide variety of forms in addition to the embodiments described above, as long as it is not beyond the scope of the present invention.

The X-ray image detecting device may be used in a visiting car that can make radiography while making rounds at sickrooms, or in a movable system that can make radiography in an accident or disaster location requiring urgent medical treatment or a private home of a home care patient, in addition to in the X-ray image capturing system installed in an X-ray room of a hospital.

In the above embodiments, the imaging control unit is separated from the X-ray image detecting device. However, the imaging control unit may be integrated into the X-ray image detecting device, in such a manner that the control unit of the X-ray image detecting device has the function of the imaging control unit.

The portable X-ray image detecting device is described in the above embodiments, but the present invention may be applied to a stationary X-ray image detecting device.

The present invention is applicable to a radiation image capturing system using another type of radiation such as y-rays, instead of the X-rays.

Although the present invention has been fully described by the way of the preferred embodiment thereof with reference to the accompanying drawings, various changes and modifications will be apparent to those having skill in this field. Therefore, unless otherwise these changes and modifications depart from the scope of the present invention, they should be construed as included therein.

What is claimed is:

1. A radiographic image detecting device comprising:
   an image detector having an imaging area having a matrix of a plurality of pixels each for accumulating signal charge in accordance with an irradiation amount of radiation emitted from a radiation source, for detecting a radiographic image by receiving said radiation passed through an object;
   a plurality of radiation detectors disposed in said imaging area, each for outputting a detection signal in accordance with said irradiation amount of said radiation; and
   a control unit for performing a synchronization control for synchronizing an operation of said image detector with emission start timing of said radiation based on said detection signal of said radiation detector, and an automatic exposure control for controlling a total irradiation amount of said radiation based on said detection signal of said radiation detector, wherein
   said detection signal of said radiation detector disposed in a first detection area in said imaging area is used in said synchronization control, and said detection signal of said radiation detector disposed in a second detection area smaller than said first detection area is used in said automatic exposure control.

2. The radiographic image detecting device according to claim 1, wherein said second detection area is included in said first detection area.

3. The radiographic image detecting device according to claim 2, wherein said control unit designates said second detection area based on said detection signals outputted from said plurality of radiation detectors disposed in said first detection area.

4. The radiographic image detecting device according to claim 3, wherein said control unit designates said second detection area by using said detection signal read in said synchronization control.

5. The radiographic image detecting device according to claim 3, said control unit compares said detection signals outputted from said plurality of radiation detectors disposed in said first detection area, and judges a section having said radiation detector that outputs a relatively low detection signal as a section opposed to said object, and designates said section opposed to said object as said second detection area.

6. The radiographic image detecting device according to claim 1, wherein said imaging area is composed of a plurality of divided sections each having said radiation detector, and said first detection area is composed of a combination of said divided sections, and said second detection area is composed of another combination of said divided sections.

7. The radiographic image detecting device according to claim 6, wherein each of said divided sections has a same number of radiation detectors.

8. The radiographic image detecting device according to claim 1, wherein in said synchronization control, said control unit monitors a start of emission of said radiation from said radiation source based on said detection signal of said radiation detector disposed in said first detection area, and makes said image detector start accumulating said signal charge upon detecting said start of emission of said radiation from said radiation source.

9. The radiographic image detecting device according to claim 8, wherein in said synchronization control, said control unit detects said start of emission, when one of said detection signals of said plurality of radiation detectors disposed in said first detection area has exceeded a threshold value.

10. The radiographic image detecting device according to claim 1, wherein in said automatic exposure control, said control unit measures a total irradiation amount of said radiation by integrating said detection signal of said radiation detector, and makes said radiation source stop emitting said radiation when said total irradiation amount has reached a threshold value.

11. The radiographic image detecting device according to claim 1, wherein when said total irradiation amount of said radiation has reached a threshold value, said control unit ends accumulation of said signal charge by said image detector.

12. The radiographic image detecting device according to claim 1, wherein in said automatic exposure control, said control unit measures a total irradiation amount of said radiation by integrating said detection signal of said radiation detector, and controls a gain in reading said signal charge from said pixel based on said total irradiation amount.

13. The radiographic image detecting device according to claim 1, wherein said radiation detector is a short pixel in which said pixel and a signal line for reading said signal charge from said pixel are always short out, and said short pixel always outputs to said signal line said signal charge in accordance with said irradiation amount of said radiation.

14. The radiographic image detecting device according to claim 1, wherein said radiation detector is a photosensor array stacked on said image detector, and said photosensor array has a plurality of detection elements for outputting said detection signal in accordance with said irradiation amount of said radiation.

15. The radiographic image detecting device according to claim 14, wherein said photosensor array is made of an organic photoelectric conversion material.

16. The radiographic image detecting device according to claim 15, wherein said photosensor array is disposed on a side of said radiation source with respect to said imaging area.

17. The radiographic image detecting device according to claim 1 allows taking a moving image, in addition to a still image.

18. The radiographic image detecting device according to claim 1, wherein said radiation source continuously emits a plurality of radiation pulses; and said control unit performs said synchronization control and said automatic exposure control on a pulse-by-pulse basis.

19. A control method of a radiographic image detecting device having an imaging area having a matrix of a plurality of pixels each for accumulating signal charge in accordance with an irradiation amount of radiation emitted from a radiation source, said radiographic image detecting device detecting a radiographic image by receiving said radiation passed through an object, said control method comprising the steps of:

performing a synchronization control for synchronizing an operation of said radiographic image detecting device with emission start timing of said radiation based on a detection signal of a radiation detector disposed in a first detection area of said imaging area; and performing an automatic exposure control for controlling a total irradiation amount of said radiation based on said detection signal of said radiation detector disposed in a second detection area smaller than said first detection area.

* * * * *